United States Patent [19]

Homma et al.

[11] Patent Number: 4,575,459

[45] Date of Patent: Mar. 11, 1986

[54] TOXOIDS OF ELASTASE OF *PSEUDOMONAS AERUGINOSA* ORIGIN

[75] Inventors: Yuzuru Homma, Tokyo; Kazuyuki Morihara, Osaka, both of Japan

[73] Assignee: Toho Yakuhin Kogyo Kabushiki Kaisha, Osaka, Japan

[21] Appl. No.: 694,637

[22] Filed: Jan. 24, 1985

[30] Foreign Application Priority Data

Feb. 24, 1984 [JP] Japan .................................. 59-35061
Feb. 24, 1984 [JP] Japan .................................. 59-35062

[51] Int. Cl.$^4$ ..................... C07G 7/00; A61K 39/40; A61K 39/104; C12P 21/00
[52] U.S. Cl. ................................. 424/87; 260/112 R; 424/85; 424/88; 424/92; 424/94; 435/68; 435/253; 435/875
[58] Field of Search ..................... 424/85, 88, 92, 177, 424/94, 87; 260/112 R; 435/68, 253, 875

[56] References Cited

U.S. PATENT DOCUMENTS

| | | | |
|---|---|---|---|
| 3,658,986 | 4/1972 | Tompkins et al. | 424/88 |
| 3,987,164 | 10/1976 | Homma et al. | 424/92 |
| 4,079,126 | 3/1978 | Homma et al. | 424/92 |
| 4,157,389 | 6/1979 | Homma et al. | 424/92 |
| 4,160,023 | 7/1979 | Homma et al. | 424/87 |
| 4,470,924 | 9/1984 | Iglewski et al. | 260/112 R |
| 4,488,991 | 12/1984 | Tolman et al. | 260/112 R |

OTHER PUBLICATIONS

J. Biol. Chem., 240:3295-3304 (1965), Morihara et al.
J. Biol. Chem., 255:3482-3486 (1980), Nishino et al.

*Primary Examiner*—Howard E. Schain
*Attorney, Agent, or Firm*—Wenderoth, Lind & Ponack

[57] ABSTRACT

Provided herein are two kinds of toxoid of elastase of *Pseudomonas aeruginosa* origin, one of which is obtained by treating a purified elastase produced from *Pseudomonas aeruginosa* with a synthetic peptide for chloroacetyl-N-hydroxy-L-leucyl-L-alanylglycinamide and the other of which is obtained by treating at first with formalin, then, with the synthetic peptide. The present invention also contemplates a method for preparing the toxoids and the use of such toxoids for preventing and treating infections caused by *Pseudomonas aeruginosa* on human beings and mammalian animals. Acute toxicity of the toxoids is inspected.

10 Claims, No Drawings

TOXOIDS OF ELASTASE OF *PSEUDOMONAS AERUGINOSA* ORIGIN

BACKGROUND OF THE INVENTION (a) Field of the Invention

This invention relates to provide novel toxoids of elastase which is originated from *Pseudomonas aeruginosa* through inactivating its virulence, in other words, any toxoidizing with a synthetic peptide reagent of chloroacetyl-N-hydroxy-L-leucyl-L-alanylglycinamide while leaving its antigenity as it is.

(b) Description of the Prior Art

*Pseudomonas aeruginosa* is gram-negative and aerobic bacillus which generally co-exist with pyogenic bacillus and is known to be a pathogen of pyothorax, tympanitis, cystitis, hemorrhagic pneumonia, etc., on human beings and mammalian animals, especially on a mink, which is known to be one of the most expensive sources of furs. In both the fields of human and veterinary medicines, so-called "Opportunistic infections" caused by *Pseudomonas aeruginosa* has recently provoked an attention among doctors as the subject to be solved urgently, and immunotherapy as well as chemotherapy using antibiotics have been carried out for preventing and treating said infections, however, they are said yet incomplete and are under development.

In regard with the above-mentioned immunotherapy, the same inventors as this invention's had reached the findings that enzyme such as elastase and protease of *Pseudomonas aeruginosa* origin possessed antigenic activity, however, they also possessed undesirable activity such as destroying the protein tissues of patients and these undesirable enzymatic activities made infectious diseases caused by *Pseudomonas aeruginosa* hard to cure.

Then, for the purpose of inactivating as above these undesirable enzymatic actions while leaving desirable antigenic actions as they are, there were provided the toxoids of elastase and protease which were respectively inactivated with formalin, and the vaccine which consisted of the abovementioned two kinds of toxoid and an antigen named OEP, which was derived from Original Endotoxin Protein, which was commonly found in more than 13 kinds of *Pseudomonas aeruginosa* strains. Production, physicochemical properties and immunological properties of the above two kinds of toxoid together with the production of purified crystalline elastase and protease, which were used as a raw material of the toxoids, were disclosed, for example, in the specification of U.S. Pat. No. 4,160,023 patented on July 3, 1979 and those of the latter vaccin were disclosed, for example, in the specification of U.S. Pat. No. 4,157,389 patented on June 5, 1979 by the same inventors as this invention's.

SUMMARY OF THE INVENTION

This invention relates to toxoids which are first prepared from purified crystalline elastase obtained from *Pseudomonas aeruginosa* by treating it with a known synthetic peptide reagent or treating it preliminarily with formalin, then, with the synthetic peptide reagent for inactivating its enzymatic proteinase activity while leaving its antigenic activity as it is. The synthetic peptide reagent herein employed is chloroacetyl-N-hydroxy-L-leucyl-L-alanylglycinamide represented by a following formula:

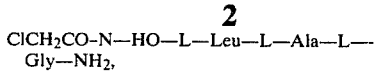

wherein Leu, Ala and Gly respectively express leucine, alanine and glycine, which is hereinafter referred to as "Powers Reagent" throughout this specification.

The novel toxoids of this invention are stable in their activity for a longer period of time than that of the toxoids of elastase which were invented and disclosed by the present inventors in U.S. Pat. No. 4,160,023, and the present toxoids are effective to prevent and treat infectious diseases caused by *Pseudomonas aeruginosa* both on human beings and mammalian animals.

DETAILED DESCRIPTION OF THE INVENTION

The afore mentioned and known toxoids were characterized by the relatively simple producing procedures, which will necessarily lower production costs, however, our recent clinical experiences have taught that an excess treatment of elastase with formalin designed to positively remove its undesirable proteinase activity, for instance, to the extent of less than 1/100 in potency of that of the original activity, may cause a sudden drop of its desirable activity simultaneously, as shown in a following Table:

TABLE 1

| Sample | Residual Proteinase Activity (%) | Antigenic Activity ($\mu$g/ml) |
|---|---|---|
| Untreated | 100 | 30 |
| Treated with HCHO (No. 1) | 8 | 30 |
| Treated with HCHO (No. 2) | 5.5 | 30 |
| Treated with HCHO (No. 3) | 1.5 | 60 |
| Treated with HCHO (No. 4) | 0.7 | 240 |
| Treated with HCHO (No. 5) | 0.3 | 480 |

Note: In the above Table 1, the antigenic activity is expressed by a unit of $\mu$g/ml, wherein the numerator indicates the quantity of antigen and the denominator indicates the dilution volume required until a precipitation line first becomes visible. So the larger the numeral is, the less potent the antigen activity.

The present invention has been attained for the purpose of improving above these defects found on the known elastase toxoids and providing stable and effective elastase toxoids.

The Powers Reagent employed in this invention as an inactivator was at first disclosed by N. Nishino and James C. Powers in the Journal of Biological Chemistry (USA), Vol. 225, No. 8, pages 3482–3486 (1980), in which Dr. Powers et al. stated that the incubation of this reagent with *Pseudomonas aeruginosa* elastase resulted in a progressive loss of enzyme activity, however, no discussions were made by them about any influences on its antigenic activity.

The physical and chemical properties of Powers Reagent are as follows:

Melting point; 65°–75° C. (Decomposition) $^1$HNMR spectrum; 9.8 (1H, b, CONCOH), 3.7 (2H, d, NHCH$_2$CO), 1.4 (3H, d, CH$_3$CH), 0.9 (6H, d, CH$_3$CH), 8.2–7.9 (2H, m, 2CONH), 7.0 (2H, d, CONH$_2$), 4.4 (2H, ClCH$_2$CO).

One of the products of this invention is a toxoid which is prepared by inactivating *Pseudomonas aerugi-*

*nosa* elastase with the Powers Reagent, hereinafter referred to as "Toxoid I", and the other product of this invention is a toxoid which is prepared by inactivating *Pseudomonas aeruginosa* elastase once with formalin then with a Powers Reagent, hereinafter referred to as "Toxoid II". These toxoids are prepared through procedures conventionally adopted in the field of protein chemistry, and the preparation of purified crystalline elastase therein used as a raw material was disclosed by one of the inventors of this invention, K. Morihara, in the Journal of Biological Chemistry (USA), Vol. 210, pages 3295–3304 (1965) in detail (cf. U.S. Pat. No. 4,160,023).

EXAMPLE

EXAMPLE 1

Preparation of Toxoid I

One hundred milligrams of crystalline elastase and 50 mg of Powers Reagent were dissolved in 100 ml of 0.1M tris-buffer solution (pH 7.0) and the solution was kept for 24 hours long at a room temperature. The reactant was dialyzed against water and the dialysate was lyophilized, then, 95 mg of toxoid which showed 0.06 mPU/mg protein of a specific activity were given.

The meaning of "mPU/mg protein of a specific activity" will be explained later in this specification.

EXAMPLE 2

Preparation of Toxoid II

A solution of 100 mg of purified crystalline elastas with or without 0.1M lysine in 0.1M phosphate buffer solution (pH 7.0) which contained 1% of formalin and the solution was kept for two days at room temperature. The reactant was dialyzed against water to remove formalin and lysine, and was concentrated with a collodion film, then, 22 ml of water solution which were equivalent to 4 mg protein/ml, of which the specific activity was equal to 3.75 mPU/mg protein (residual activity 7.5%).

To the thus-formed solution, 22 ml of 0.2M tris-buffer solution (pH 7.0) which dissolved 8 mg of Powers Reagent were added and the mixed solution was kept for 3 days at room temperature and was dialyzed against water and was lyophilized, then, 80 mg of toxoid, which were equivalent to 1/500 of the activity which the original crystalline elastase possessed, were given.

Moreover, under the same experimental conditions as the above, the formalin-inactivated elastases were respectively treated with each 2, 1, 0.5 and 0.1 mgs of Powers Reagent, then, there were respectively given 80–85 mg of the toxoids, each of which possessed 0.15, 0.2, 0.3 and 0.6 mPU/mg protein of a specific activity.

From the result thus observed in Example 2, it is recommended, from a practical viewpoint, that to provide such a toxoid which possesses a proteinase activity of less than 1/500 of that of an original crystalline elastase, the elastase should be treated with 1% of formalin solution so as to decrease its proteinase activity into 1–10%, preferably around 5%, of that of the original elastase and then a Powers Reagent is added in a quantity of corresponding to the thus remained active elastase in which 50 mPU correspond to 1 mg of elastase.

Further, in comparison of the above Example 1 with Example 2, it must be noted that the quantity of Powers Reagent in respect to 100 mg of the material crystalline elastase is as much as 50 mg in the Example 1 and 8 mg in Example 2. As the Powers Reagent is a relatively expensive substance, the latter Toxoid II is more advantageous in production cost than the former Toxoid I when they are produced massively. On the other hand, the biological and immunological properties are almost equal to each other.

In Examples 1 and 2, the term "mPU/ml protein of a specific activity" signifies the proteinase activity determined by the following procedure:

Casein (2%, pH 7.4, 1 ml) is admixed with 1 ml of an appropriately diluted solution of an enzyme, and after a reaction at 40° C. for 10 minutes, 2.0 ml of a solution containing 0.1M trichloroacetic acid and 0.2M sodium acetate is immediately added for stopping a progress of the reaction. The mixture is kept at the same temperature for 20 minutes to precipitate unreacted casein completely and is filtered. 1 ml of the filtrate is subject to determination of tyrosine therein contained by the Folin's method. By the increase of $1\gamma$ of tyrosine per 1 minute, a proteinase activity of 1 mPU is to be indicated. 1 mPU × 1,000 is equal to 1 PU.

The physical and chemical properties of Toxoid I have been identified following:

(1) Molecular weight: 20,400 (determined by a method of SDS-polyacrylamide gel cataphoresis).

(2) Ultraviolet absorption spectrum: Maximum 280 nm ($E_1^{280}\% = 14.52$, pH 10), Minimum 252 nm.

(3) Isoelectric point: pH 7.0 (determined by a cataphoresis with an acetate film).

(4) Composition of amino acids: Amino acid residues (mol protein) Aspartic acid (15.7), Threonine (6.9), Serine (9.2), Glutamic acid (6.3), Proline (4.5), Glycine (13.5), Alanine (11.0), cystine/2 (1.6), Valine (6.7), Methionine (3.0), Isoleucine (3.0), Leucine (5.4), Tyrosine (8.2), Phenylalanine (6.3), Lysine (4.4), Histidine (2.5), Arginine (5.9), Tryptophane (3.0) (Total 117.1 residues).

(5) Color: Colorless powders (6) Antigenic activity: Positive (7) Enzymatic activity: Negative, and the chemical and physical properties of Toxoid II have been identified followingly;

(1) Molecular weight: 23,300 (determined by a method of SDS-polyacrylamide gel cataphoresis)

(2) Ultraviolet absorption spectrum: Maximum at 280 nm ($E_1^{280}\% = 11$, pH 10), Minimum at 252 nm (3) Isoelectric point: pH 6.0 (determined by a cataphoresis with an acetate film).

(4) Composition of amino acids: Amino acid residues (mol protein) Aspartic acid (18.1), Threonine (7.9), Serine (10.6), Glutamic acid (7.3), Proline (5.2), Glycine (14.7), Alanine (11.8), Cystine/2 (1.8), Valine (7.8), Methionine (3.5), Isoleucine (3.8), Leucine (6.1), Tyrosine (1.6), Phenylalanine (7.1), Lysine (8.7), Histidine (3.7), Arginine (7.0), Tryptophane (3.5) (Total: 130.2 residues)

(5) Color: Colorless powders (6) Antigenic activity: Positive (7) Enzymatic activity: Negative

EXPERIMENT

Immunological properties of Toxoid I and Toxoid II of this invention will be demonstrated by the following experimental data:

EXPERIMENT 1

Antigenicity Test on Rabbits

Method: Three rabbits, each having 2.5 Kg of a body weight, were subcutaneously inoculated with each 1 mg of Toxoid I together with Freund's incomplete adjuvant and the inoculation was repeated 3 to 4 times at an interval of 2 weeks. On the day of two weeks after the last inoculation, blood was collected from the rabbits and was availed for following Tests A, B and C. The same method as the preceeding was conducted employing Toxoid II.

TEST A

Passive Hemagglutinative Value Test (PHA Test)

The values were determined according to a method described by one of the present inventors, Y. Homma, in The Japan J. Exp. Med., Vol. 45, No. 5, pages 361-365 (1975), and the values were expressed as a reciprocal number to a multiplied number of the dilution of sera.

Results:

| PHA Value | | | |
|---|---|---|---|
| Toxoid I | | Toxoid II | |
| (Rabbit No. 1) | 5120 | (Rabbit No. 4) | 5110 |
| (Rabbit No. 2) | 2560 | (Rabbit No. 5) | 2560 |
| (Rabbit No. 3) | 2560 | (Rabbit No. 6) | 2550 |

Note: Before the first inoculation, No elastase PHA value was observed.

TEST B

Precipitation in Agar-gel Test

In 0.01M phosphate buffer-normal saline solution (pH 7.0) which contained 0.1% of sodium azide, agarose was dissolved to form a concentration of 1.5% by weight, and 10 ml of the solution were poured in a dish having 9 cm of a diameter and the solution was left to make the agar hard. Several holes were made on the hardened agar and antigens or antisera were separately poured into every hole and the agar was left at 22° C. for 24 hours long, then, the existence of a precipitation line was inspected. The concentration of antigens is expressed by a unit of $\mu g/ml$, wherein the numerator indicates a quantity of antigens and a denominator indicates the dilution volume which is required until a precipitation line will first becomes observable.

Results:

| Antigen Concentration ($\mu g/ml$) | | | |
|---|---|---|---|
| Toxoid I | | Toxoid II | |
| (Rabbit No. 1) | 15 | (Rabbit No. 4) | 15 |
| (Rabbit No. 2) | 15 | (Rabbit No. 5) | 15 |
| (Rabbit No. 3) | 15 | (Rabbit No. 6) | 15 |

Note: The same test as the preceeding employing an authentic crystalline elastase also resulted in a concentration of 15 $\mu g/ml$.

TEST C

Elastase-neutralizing Activity Test

Sera of the tested rabbits were warmed at 56° C. for 30 minutes and 0.2 ml of the sera were added to 0.2 ml of elastase solution, to which normal saline solution was added up to a volume of 2 ml in total. The solution was left for 60 minutes at 37° C., then, 1 ml of 2% casein solution was added to 1 ml of the solution. The residual elastase activity was determined with the thus mixed solution. Values of an elastase activity with which 1 ml of anti-serum could be neutralized were demonstrated as follows:

Results:

| Elastase-neutralizing Activity (mPU/ml) | | | |
|---|---|---|---|
| Toxoid I | | Toxoid II | |
| (Rabbit No. 1) | 15 | (Rabbit No. 4) | 15 |
| (Rabbit No. 2) | 12 | (Rabbit No. 5) | 13 |
| (Rabbit No. 3) | 10 | (Rabbit No. 6) | 11 |

EXPERIMENT 2

PHA and Elastase-neutralizing Activity on Mice

To a solution of Toxoid I of this invention in a concentration of 0.5 mg/ml., an equal volume of 1% potassium alum solution was added. Each 0.2 ml of the solution, in which 50 $\mu g$ of Toxoid I were contained, were inoculated into ddY mice of 4 weeks old respectively three times at an interval of 2 weeks. At just before and on the 14th day after the third inoculation, bloods were collected from each mouse and the values of PHA and elastase-neutralizing activity were inspected in the same manner as with Tests A and C in Experiment 1.

The PHA value was commonly 640 with the first and the second collected bloods and the value of elastase-neutralizing activity was 1.52 mPU/ml with the first collected-blood and 1.83 mPU/ml with the second collected-blood.

The toxoid II of this invention was treated in the same manner as above, which resulted commonly in a PHA value of 640 with the first and the second collected-blood and the value of the elastase-neutralizing was 1.55 mPU/ml with the first collected blood and 1.80 mPU/ml with the second collected blood.

EXPERIMENT 3

Antigen Activity on Minks

Two groups, each consisted of twenty or more Sapphire minks, were subcutaneously inoculated with each 500 $\mu g$ Toxoid I or Toxoid II together with an adjuvant of potassium alum for vaccinization. Two weeks later, each 500 $\mu g$ of Toxoid I or Toxoid II were inoculated with the adjuvant similarly to the first inoculation. Further, three weeks after the second inoculation, each 1,000 $\mu g$ of Toxoid I or Toxoid II were subcutaneously inoculated. On the 18th day from the last inoculation, every mink was drawn of its blood.

In most of the sera of the thus drawn bloods, an increase in PHA value of 16 to 60 fold of the original value was commonly observed.

From the results obtained from the above experiments, it was confirmed that injections of Toxoid I or Toxoid II of this invention may result in the prominent elevation of the PHA value and an antigen-neutralizing activity.

With respect to the acute toxicity of Toxoid I and Toxoid II of this invention, a $LD_{50}$ value has been commonly determined through an intraperitoneal administration on mice to be more than 1 mg/Kg of a body weight, while crystalline elastase of *Pseudomonas aeru*- ginosa origin is 0.125 mg/Kg of the body weight of a mouse.

Consequently, Toxoid I and Toxoid II of this invention are available, by themselves or together with pharmaceutically acceptable excipients as a pharmaceutical agent, for the production of antibodies or anti-sera, and they are useful for preventing and treating infectious diseases caused by *Pseudomonas aeruginosa* on human beings and mammalian animals.

To explain some practical uses of the toxoids of this invention, tested minks were divided into two groups, one was infected with *Pseudomonas aeruginosa* and the other was kept uninfected. Both of the group were treated with vaccine which was composed of the three components for the toxoid of this invention, a separately prepared protease toxoid from *Pseudomonas aeruginosa* and the foregoing explained OPE (cf. for example, U.S. Pat. No. 4,157,389), wherein, two groups of minks exhibited almost the same survival ratio, while there was found to be no survivals with a control group of minks which was infected but untreated with the vaccine.

Further, the vaccine will be preferably available for prevention and treatment of chronic infectious diseases caused by *Pseudomonas aeruginosa* which are generally said to be uncurable by the administration of antibiotics only, and acute *Pseudomonas aeruginosa* infectious diseases such as burns.

What we claim is:

1. A toxoid of the elastase of *Pseudomonas aeruginosa* origin, which is obtained by treating purified elastase produced from *Pseudomonas aeruginosa*, for inactivating the activity of proteinase naturally existing in the purified elastase, in a buffer solution with a synthetic peptide of chloroacetyl-N-hydroxy-L-leucyl-L-alanyl-glycinamide represented by the following formula:

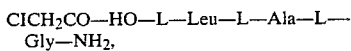

wherein Leu, Ala and Gly express respectively leucine, alanine and glycine, in a proportion of 40-60% by weight of the purified elastase, with subsequent steps of dialysis and lyophilization, said toxoid possessing the following physicochemical properties:
  (1) Molecular weight: 20,400, determined by a method of SDS-polyacrylamide gel cataphoresis,
  (2) Ultraviolet absorption spectrum: maximum at 230 nm, ($E_1^{280}\% = 14.52$, pH 10), minimum at 252 nm,
  (3) Isoelectric point: pH 7.0, determined by cataphoresis with an acetate film,
  (4) Composition of amino acids: amino acid residues (mol protein) aspartic acid (15.7), threonine (6.9), serine (9.2), glutamic acid (6.3), proline (4.5), glycine (13.5), alanine (11.0), cystine/2 (1.6), valine (6.7), methionine (3.0), isoleucine (3.0), leucine (5.4), tyrosine (8.2), phenylalanine (6.3), lysine (4.4), histidine (2.5), arginine (5.9), and tryptophane (3.0) (Total 117.1 residues),
  (5) Color: colorless powders,
  (6) Antigen activity: positive, and
  (7) Enzymatic activity: negative.

2. A toxoid of elastase of *Pseudomonas aeruginosa* origin, which is obtained by treating purified elastase produced from *Pseudomonas aeruginosa*, for inactivating the activity of proteinase naturally existing in the purified elastase in a buffer solution, at first with formalin to decrease its proteinase activity to the extent of 1-10% of that of the purified elastase possessed originally, then, by treating with a synthetic peptide of chloroacetyl-N-hydroxy-L-leucyl-L-alanylglycinamide represented by a following formula:

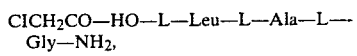

wherein Leu, Ala and Gly express respectively leucine, alanine and glycine, to decrease its thus remaining proteinase activity to the extent of less than 1/500 of that of the purified elastase possessed originally, with subsequent steps of dialysis and lyophilization, said toxoid possesses following physicochemical properties:
  (1) Molecular weight: 23,300, determined by a method of SDS-polyacrylamide gel cataphoresis,
  (2) Ultraviolet absorption spectrum: maximum at 280 nm, ($E_1^{280}\% = 11$, pH 10), minimum at 252 nm,
  (3) Isoelectric point: pH 6.0, determined by cataphoresis with an acetate film,
  (4) Composition of amino acids: amino acid residues (mol protein) aspartic acid (18.1), threonine (7.9), serine (10.6), glutamic acid (7.3), proline (5.2), glycine (14.7), alanine (11.8), cystine/2 (1.8), valine (7.8), methionine (3.5), isoleucine (3.8), leucine (6.1), tyrosine (1.6), phenylalanine (7.1), lysine (8.7), histidine (3.7), arginine (7.0), tryptophane (3.5); total 130.2 residues,
  (5) Color: colorless powders,
  (6) Antigen activity: positive, and
  (7) Enzymatic activity; negative.

3. A method for preventing infections caused by *Pseudomonas aeruginosa* through inoculating the toxoid claimed in claim 1 in a sufficient quantity to produce an anti-elastase antibody.

4. A method for preventing infections caused by *Pseudomonas aeruginosa* through inoculating the toxoid claimed in claim 2 in a sufficient quantity to produce an anti-elastase antibody.

5. An anti-serum for preventing and treating infections caused by *Pseudomonas aeruginosa*, which is obtained from human or animal serum by inoculating the toxoid claimed in claim 1.

6. An anti-serum for preventing and treating infections caused by *Pseudomonas aeruginosa*, which is obtained from human or animal serum by inoculating the toxoid claimed in claim 2.

7. The toxoid according to claim 1, wherein the buffer solution is at a pH of 7.0.

8. The toxoid according to claim 2, wherein the buffer solution is at a pH of 7.0.

9. The toxoid according to claim 1, wherein the synthetic peptide is employed in a proportion of 50% by weight of the purified elastase.

10. The toxoid according to claim 2, wherein the decrease of proteinase activity by treating with formalin is 7.5% of that of the purified elastase possessed originally and the final proteinase activity by treating with the synthetic peptide is 1/500 of that of the purified elastase possessed originally.

* * * * *